United States Patent [19]

VanderLaan

[11] Patent Number: 4,585,740
[45] Date of Patent: Apr. 29, 1986

[54] PROLACTIN IMMUNOASSAY USING SYNTHETIC PEPTIDE

[75] Inventor: Willard P. VanderLaan, La Jolla, Calif.

[73] Assignee: The Whittier Institute for Diabetes and Endocrinology, La Jolla, Calif.

[21] Appl. No.: 491,059

[22] Filed: May 3, 1983

[51] Int. Cl.[4] .................. G01N 33/54; G01N 33/56; A61K 37/02
[52] U.S. Cl. ............................ 436/537; 260/112.5 R; 424/1.1; 424/85; 424/88; 514/14; 435/4; 435/7; 436/542; 436/545; 436/547; 436/804; 436/817; 436/822; 436/823
[58] Field of Search ................. 260/112.5 R; 436/510, 436/536–540, 542, 543–546, 547, 822, 804, 814, 817, 823; 435/4, 7; 424/1.1, 85, 88, 177

[56] References Cited

U.S. PATENT DOCUMENTS

| 4,189,426 | 2/1980 | Li | 260/112.5 R |
| 4,201,770 | 5/1980 | Stevens | 260/112.5 R |
| 4,202,802 | 5/1980 | Shields | 260/112.50 S |
| 4,302,386 | 11/1981 | Stevens | 260/112.5 R |
| 4,357,310 | 11/1982 | Chan et al. | 436/504 |
| 4,384,995 | 5/1983 | Stevens | 260/112.5 R |

OTHER PUBLICATIONS

Biochemical Biophysical Research Communication, vol. 115(1), pp. 346–350, (1983), VanderLaan, W. P. et al.
Journal of Biological Chemistry, vol. 255(23), pp. 11478–11483, (1980), Majzoub, J. A. et al.
Endocrinology, vol. 110(6), pp. 1871–1878, (1982), Sinha, Y. N. et al.
Review Pediatrics Obstetrics Gynecology, vol. 31(1), pp. 49–58, (1983), Luca, V. et al.
Clinical Chemistry, vol. 28(7), p. 1613, (1982), Heser, D. et al.
Vestn Akad Med Mavk USSR (9), pp. 60–69, (1976), Pankov, Y. A.
Cooke, N. E. et al., J. Biol. Chem. vol. 256, pp. 4007–4016, (1981).
Sinha, Y. N. et al., J. of Clin. Endocrinology & Metabolism, vol. 36, No. 3, Mar. 1973, pp. 509–516.
Das, R. E. G. et al., J. of Endocrinology, (1979), vol. 80., pp. 157–168.

Primary Examiner—Thomas G. Wiseman
Assistant Examiner—M. Moskowitz
Attorney, Agent, or Firm—Fitch, Even, Tabin & Flannery

[57] ABSTRACT

A peptide having the formula

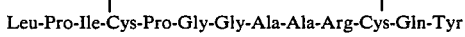

Leu-Pro-Ile-Cys-Pro-Gly-Gly-Ala-Ala-Arg-Cys-Gln-Tyr is synthesized. The peptide is conjugated, e.g., with bis-diazotized benzidine, at its C-terminus to a carrier, such as bovine serum albumin, to form a synthetic antigen useful for inducing antibody production in a host animal. The antiserum obtained from the host animal is free of cross-reactivity with other pituitary substances and thus particularly advantageous for assay purposes. The peptide, whether unlabeled or labeled with radioactive iodine on the tyrosine moiety, has an affinity to antiserum raised against the conjugate similar to the affinity of natural hPRL to the antiserum. The synthetic peptide is used in radioimmunoassays where the labeled peptide competes for the binding sites in the antiserum with unknown concentrations of hPRL in biological samples.

17 Claims, 2 Drawing Figures

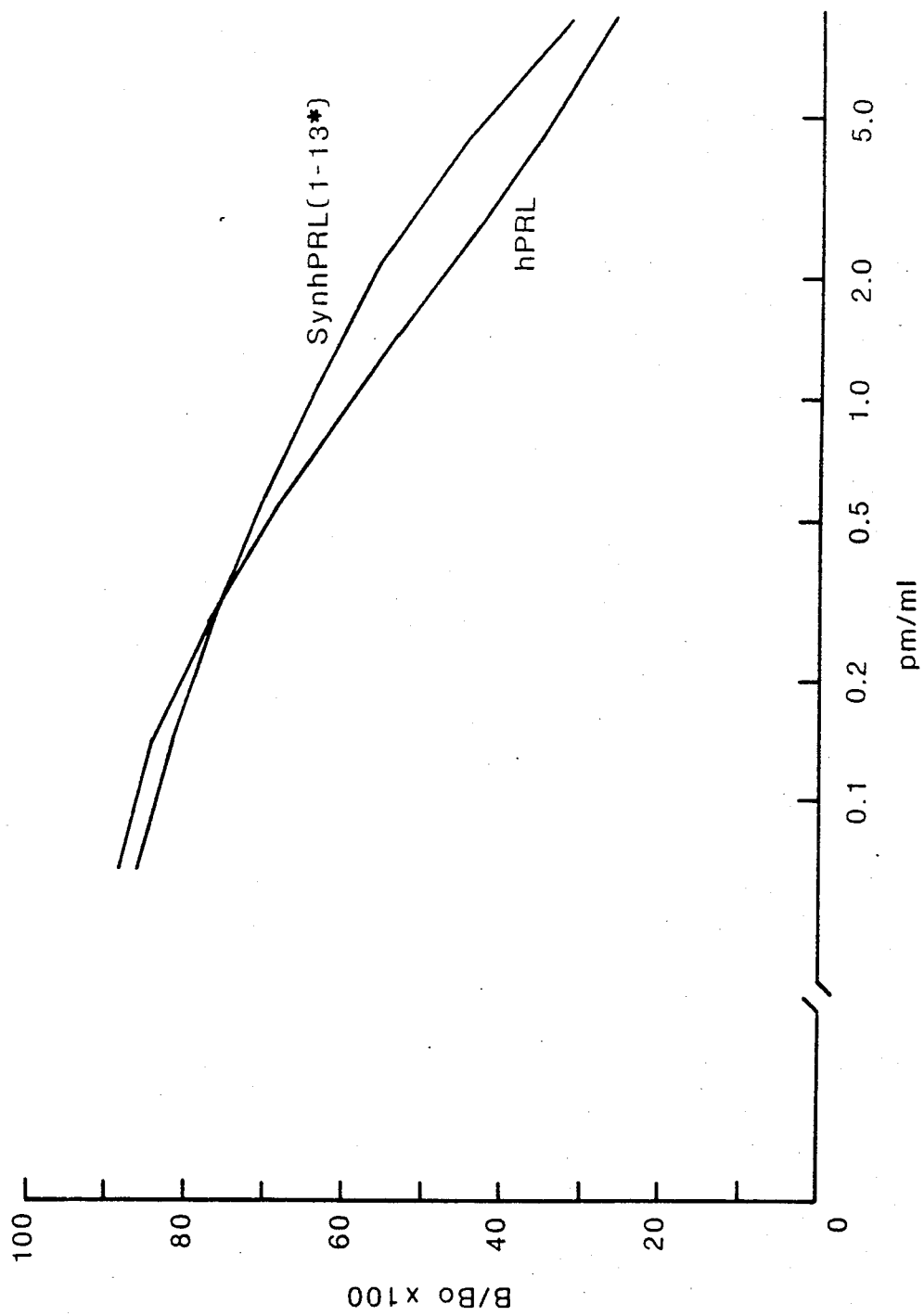
FIG. 1 Standard Displacement Curves

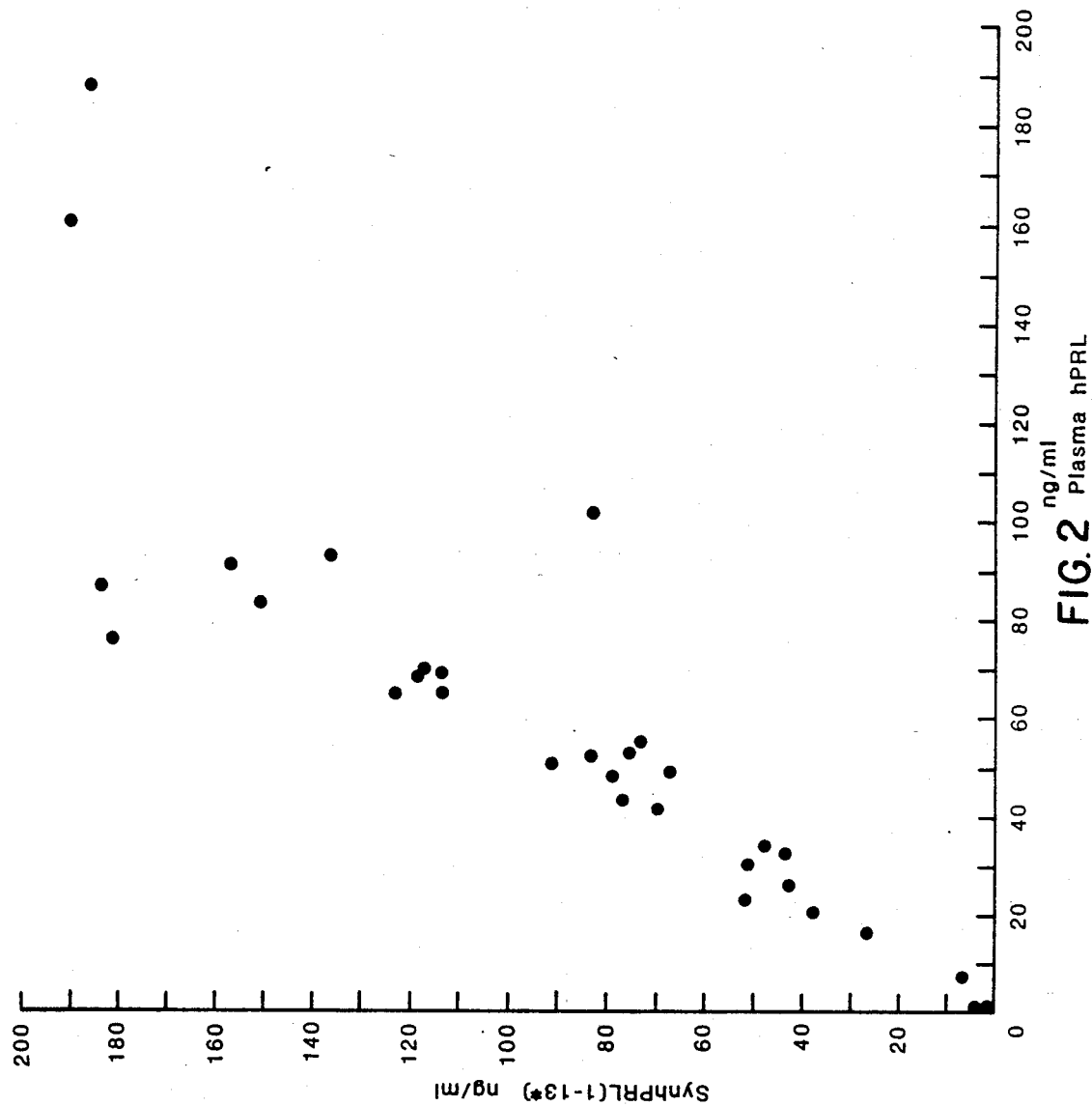

PROLACTIN IMMUNOASSAY USING SYNTHETIC PEPTIDE

This invention was made with Government support under Grant No. CA-33615-01 awarded by the Department of Health and Human Services (the National Institutes of Health). The Government has certain rights in this invention.

The present invention relates to to synthetic proteins which can be used to induce production of antibodies to a portion of human prolactin by an animal's immune system and which can be substituted for natural human prolactin in assays for human prolactin.

BACKGROUND OF THE INVENTION

Prolactin is a hormone that is produced in the anterior lobe of the pituitary gland and derives its name from its role in the initiation of lactation. Other possible regulatory functions of prolactin are not entirely clear. Prolactin is produced in both males and females and is present in elevated levels in pregnant and lactating females and in patients with prolactin-secreting pituitary tumors.

Human prolactin (hPRL) is a hormone comprising a single protein chain with a molecular weight of about 23,000. Its structure has been elucidated and published, Cook et al., J. Biol. Chem., 256:4007–4016 (1981).

A radioimmunoassay, which has become a standard assay for determining hPRL levels in biological samples, was described in Sinha, et al., J. Of Clin. Endocrinology & Metabolism, Vol. 36, No. 3, March 1973, pp. 509–516. This immunoassay uses hPRL obtained from pituitary glands of recently deceased persons as standards for assays, as labeled peptide in the radioimmunoassay and to induce production of antibody to hPRL in host animals. Not only is obtaining hPRL from its natural source a continuous problem, but human prolactin must be isolated and substantially purified by relatively tedious procedures. The activity of the isolated prolactin must then be determined on a lot-by-lot basis.

Furthermore, when hPRL is obtained from human pituitary glands, it is invariably contaminated with other pituitary substances, including other hormones. This poses problems in the production of antisera because antisera induced by even a slightly impure prolactin fraction contain antibodies to the contaminating pituitary substances. With careful purification, such contamination can be minimized; for example, the antiserum described in Sinha et. al. supra. publication had less than two percent cross-reactivity with human growth hormone. However, high purity hPRL is isolated only with the exercise of great care but with low yield, and the cross-reactivity of antisera for interfering substances must be determined on a lot-by-lot basis.

Thus while the previously described assay for hPRL is sensitive and has gained widespread acceptance, its accuracy is subject to the careful performance of preparatory and quantitative procedures. It would be desirable to have a radioimmunoassay for hPRL which does not require human pituitary extracts and which is less dependent on careful prior isolation and prior quantitation. Further, highly purified hPRL is difficult to iodinate, and radioiodinated hPRL tends to be unstable.

SUMMARY OF THE INVENTION

A radioimmunoassay for human prolactin (hPRL) has now been developed which utilizes a synthetic peptide. When conjugated to a large carrier protein, such as bovine serum albumin, and injected into a host animal, the peptide portion of the conjugate induces an immune response that results in the animal generating an antiserum useful for hPRL assays.

The synthetic peptide by itself is used in immunoassays where it competes for the hPRL binding sites of antibody raised against the conjugate. The synthetic peptide can be labeled with a radioactive isotope, such as a radioactive iodine, so that it serves as a marker in a radioimmunoassay.

In a typical assay, standard concentrations in increasing amounts of hPRL and/or synthetic peptide are incubated with a dilute antiserum fraction containing antibodies raised against the conjugate of the synthetic peptide. Body fluid samples containing unknown quantities of hPRL are incubated with antibody-containing serum side-by-side with the standard concentration incubation mixtures. Thereafter, radioactively labeled synthetic peptide is added to the incubation mixtures so that the labeled synthetic peptide fills unoccupied binding sites on the antibody and/or displaces some hPRL or unlabeled synthetic peptide from the antibody binding sites. Antibody-bound labeled synthetic peptide is separated from unbound labeled synthetic peptide, e.g., by filtration of the mixture through charcoal. A curve based on the amount of bound and unbound labeled peptide is prepared from the standard reaction mixtures, and the amounts of hPRL in the body fluid samples is determined by the measured amounts of bound and unbound labeled peptide as related to the standard curve.

When the synthetic peptide conjugate is used for inducing the production of antibodies, antisera generated by the host animal are free of other antibodies specific to interfering pituitary hormones.

BRIEF DESCRIPTION OF THE DRAWINGS

FIG. 1 shows a pair of standard curves generated from actual experimental data of hPRL assays in which radioactively labeled synthetic peptide is used to displace (1) hPRL and (2) unlabeled synthetic peptide from the binding sites of rabbit antiserum raised against the synthetic peptide conjugated to bovine serum albumin; and FIG. 2 plots hPRL levels of assays of 36 human blood serum samples comparing results based on the two standard curves of FIG. 1. The hPRL concentration of the samples, derived by the hPRL curve of FIG. 1, is shown on the abscissa and the hPRL concentration of the samples, derived by the synthetic peptide curve of FIG. 1, is shown on the ordinate.

DETAILED DESCRIPTION OF THE PREFERRED EMBODIMENT

In accordance with the present invention, a synthetic peptide is produced that closely corresponds in structure to a segment of hPRL and which simulates certain activity of hPRL both in vitro and in vivo. When the synthetic peptide is conjugated to a larger carrier molecule, it simulates the antigenic activity of hPRL in that, when injected into a host mammalian animal, it induces the animal's immune system to produce antibody directed against the hPRL segment to which the synthetic peptide corresponds. Because the synthetic peptide is free of other pituitary substances, antisera induced by the synthetic peptide conjugate do not exhibit cross-reactivity with other human pituitary substances.

The synthetic peptide by itself is reactive with the binding site of antibody directed against the corresponding hPRL segment and is therefore useful for in vitro immunoassays where the peptide competes with natural hPRL in body fluid samples for binding sites on hPRL antibody.

In a preferred embodiment, the peptide segment has 13 amino acid residues, including the 12 residues of the amino terminus of the natural hPRL molecule plus tyrosine at its carboxyl terminus. For inducing antibodies, the peptide is conjugated with bovine serum albumin (BSA), as by means of a bis-diazotized benzidine bridge.

Normal hPRL and the synthetic peptide have similar affinities to antisera raised against the synthetic peptide-carrier conjugate, and hPRL and the synthetic peptide compete on a generally equal basis for the binding sites of the conjugate-induced antibody and are mutually capable of displacing each other at the antibody binding sites. This characteristic of the synthetic peptide allows for reliable immunoassays in which synthetic peptide competes with hPRL in a biological sample for antibody binding sites in antiserum. For the same reason, the synthetic peptide can replace natural hPRL as an assay standard, and because its purity and stability can be more readily assured than can the purity and stability of hPRL, it is a more reliable standard than natural hPRL.

A thirteen amino acid peptide is synthesized having the following formula:

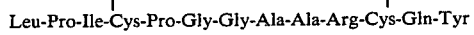

Leu-Pro-Ile-Cys-Pro-Gly-Gly-Ala-Ala-Arg-Cys-Gln-Tyr (hereinafter syn-hPRL) (all amino acids having optical isomers being of the L configuration) with Leu at the N-terminus and Tyr (free acid) at the C-terminus. The amino acids are designated by their commonly accepted three letter abbreviations: Leu=leucine, Pro=proline, Ile=isoleucine, Cys=cystine, Gly=glycine, Ala=alanine, Arg=arginine, Gln=glutamine and Tyr=tyrosine. When the carboxyl group of the Tyr residue of the peptide chain is linked with a bis-diazotized benzidine bridge to BSA, an antigenically active conjugate is formed having the formula

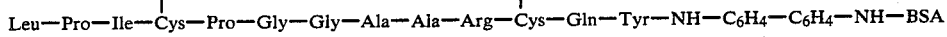

Leu—Pro—Ile—Cys—Pro—Gly—Gly—Ala—Ala—Arg—Cys—Gln—Tyr—NH—C$_6$H$_4$—C$_6$H$_4$—NH—BSA (hereinafter syn-hPRL-BSA), which when injected into a host animal induces antibodies directed against syn-hPRL and the corresponding site of natural hPRL.

The first twelve amino acid residues of syn-hPRL directly correspond to the N-terminal segment of the hPRL molecule. It may not be necessary that the entire corresponding 12 amino acid sequence be synthesized, and peptides containing an antigenically active portion of the 12 amino acid sequence may be adequate for purposes of the present invention. Generally it is considered that at least four amino acids are required for immunogenic recognition, and in this case, it is felt that the disulfide linkage between the cystines at the 4 and 11 positions contributes significantly to simulation of the natural configuration of the hPRL segment.

Tyrosine does not occupy the 13 position in the corresponding segment of the hPRL molecule but is added in the 13 position of the preferred form of syn-hPRL for two reasons: (1) because tyrosine is readily iodinated, it can be labeled with radioactive iodine, such as $^{125}$I, to serve as a radioactively labeled peptide and (2) the peptide may be easily linked through the tyrosine residue to a large carrier protein.

The carrier serves the function of enlarging the size of the synthetic peptide to where it is readily recognized by the mammalian immuno system to which the conjugate (syn-hPRL-carrier) is introduced. A molecule of a relatively large size may be necessary to induce effective antibody production, and in this regard, the carrier should preferably have a molecular weight of more than about 50,000. Bovine serum albumin has a suitable molecular weight, is readily available and is relatively inexpensive; and hence, BSA is suitable for forming synthetic antigens according to the present invention. However, other carrier molecules, such as long peptide chains of short, repeating amino acid sequences, may function equally well as carriers.

Syn-hPRL is synthesized by known peptide synthesis techniques, such as the solid-phase technique earlier developed by Merrifield, R. B., J. Am. Chem. Soc. 85:2149–2154 (1963) as described in U.S. Pat. No. 4,316,891, issued Feb. 23, 1982 to Guillemin et al., the teachings of which are incorporated herein by reference.

Syn-hPRL-BSA conjugate is formed by linking syn-hPRL to BSA with bis-diazotized benzidine, by an adaptation of the method for linking bovine thyroglobulin of Guillemin et al. Biochem, Biophys. Res. Commun. 77, 361, (1977).

Syn-hPRL is labeled with $^{125}$I using Enzymobeads and Enzymobead radioiodination reagent (Bio-Rad Laboratories, Richmond, CA). The radioiodinated syn-hPRL (hereinafter labeled syn-hPRL) is purified over a column of Sephadex G-25.

Antiserum to syn-hPRL is raised in rabbits by the method of Sigel et al., in *Methods in Enzymology*, Part E, "Immunological Techniques" 93:3–12, van Vunakis, H. and Langone, J. J. (eds.), Academic Press (1983). Syn-hPRL-BSA conjugate is emulsified in Freund's complete adjuvant and, in dosages of 150 μg, injected into the exposed retropopliteal lymph nodes of the hind limbs of three New Zealand male rabbits. Two additional subcutaneous immunizing doses of the same amount of conjugate but in incomplete adjuvant is administered fortnightly starting one month later.

The selection of the antiserum to be used is made by testing binding of the labeled syn-hPRL to dilutions of antisera collected from the ear arteries of the rabbits two weeks after the third immunization. The antisera initially are tested at 1:100, 1:1000 and 1:10,000 dilutions. Separations of bound and free labeled peptide is made by the charcoal method of Herbert et al. *J. Clin. Endocrinol. Metab.* 25:1375–1384 (1965) with the current modification that dextran is omitted.

Immunoassays using syn-hPRL and an antiserum raised against syn-hPRL-carrier are generally based upon competition for the available binding sites of the antibody, and immunoassays may be performed in several manners, including simultaneous exposure of an hPRL-containing sample and syn-hPRL to antisera or subsequent addition of either the syn-hPRL or the hPRL-containing sample. In a competition immunoassay technique, the antigenic substance in a sample of fluid being tested for its presence competes with a known quantity of labelled antigen for a limited quantity of antibody binding sites. Thus, the amount of labeled antigen bound to the antibody is inversely proportional to the amount of antigen in the sample. The relative amounts of syn-hPRL and hPRL bound to the antisera are detected by a marker, which might be a fluorescent marker or any other marker useful in immunoassays, bound to syn-hPRL; however, a radioactive marker, such as $^{125}I$ is most convenient and thus preferred.

Competitive or displacement antiserum binding reactions using unknown biological samples plus labeled syn-hPRL are carried out simultaneously with competitive or replacement antiserum binding reactions using a series of either known standard concentrations of hPRL plus labeled syn-hPRL or known standard concentrations of unlabeled syn-hPRL plus labeled syn-hPRL. A means is provided for separating antibody-bound labeled syn-hPRL from unbound labeled syn-hPRL in each reaction mixture. From the series of reaction mixtures with either standard hPRL or with standard syn-hPRL concentrations, a standard curve is plotted correlating bound and unbound labeled syn-hPRL to the concentration of the standard. The concentration of hPRL in the unknown samples can then be determined by relating the bound and unbound syn-hPRL in each reaction mixture to the standard curve.

In a preferred radioimmunoassay procedure, the biological samples and the standard series of either unlabled syn-hPRL or hPRL are preincubated with an antiserum raised against syn-hPRL-BSA for a period of a few days, e.g., three days. Labeled syn-hPRL is then added to each reaction mixtures, and the combined mixture incubated for at least one day so that the labeled syn-hPRL fills up unfilled hPRL binding sites in the antiserum and displaces some of the bound hPRL or unlabeled syn-hPRL. The reaction mixtures are passed over charcoal using the method of Herbert et al. supra. in which relatively small molecules, such as syn-hPRL, are adsorbed on the charcoal while large molecules, such as the antibody, remain in the supernatent. The amount of bound and unbound labeled syn-hPRL is determined from radioactivity counts of the supernatent and/or charcoal.

The invention will now be more fully described by way of Example of an actual radioimmunoassay that is conducted using the above-described rabbit antiserum raised against syn-hPRL-BSA and also using both labeled and unlabeled syn-hPRL.

EXAMPLE

A diluent is prepared consisting of 0.2 g BSA and 1.0 ml normal goat serum which is brought to a volume of 100 ml with veronal buffer (9.18 g sodium barbital, 1.48 g. barbital, 0.1 g sodium azide in 1.0 L water, pH 8.6). A standard series of both hPRL (obtained from the National Hormone and Pituitary Program, NIH hPRL-VLS$_4$) and syn-hPRL are diluted in diluent to 0.07, 0.14, 0.27, 0.54, 1.09, 2.18, 4.35, and 8.70 pMoles/ml. $^{125}I$-labeled syn-hPRL is prepared to 10,000 counts per minute per 100 ul in diluent. Stock antiserum, previously diluted 1:1000, is further diluted in diluent to 1:7000.

50 μl of each standard or sample is mixed with 350 μl of diluted antiserum and incubated at 4° C. for 72 hours. As a control for non-specific binding, an additional mixture containing 400 ul of diluent is incubated.

After this 72 hour incubation period, 100 ul of labeled syn-hPRL in diluent is added to each tube, and the combined mixtures (total volume 0.5 ml) are incubated for an additional 24 hours at 4° C.

A charcoal suspension is prepared consisting of 10 ml normal bovine serum and 12.5 g activated charcoal, sold under the trademark Norit A, in 500 ml acetate buffer (1.47 g sodium barbital, 0.97 g sodium acetate, 7.65 g sodium chloride, 5.0 ml 1.0 N HCl and water to 1.0 L). The charcoal suspension is stirred for 20 min. prior to use, and stirring is continued as 2.0 ml of the charcoal suspension is dispensed to each 0.5 ml reaction mixture. The combined charcoal suspension and reaction mixtures are vortexed for two to three seconds and incubated for 20 min. at room temperature. The combined mixture is then centrifuged at 2000 r.p.m. for 30 min at 20° C., and the supernatent, which represents the bound fraction, is decanted and counted in a scintillation counter.

FIG. 1 shows two standard curves for displacement by labeled syn-hPRL of (1) syn-hPRL and of (2) hPRL, plotted as log dose of the standard in picomoles/ml on the abscissa and B/Bo on the ordinate. In the expression, B/Bo, B=(B'-NSB)/(T-NSB) of each test material and Bo=(Bo'-NSB)/(T-NSB) of the zero dose level after correcting for non-specific binding, NSB. Here, B'=actual measured counts/min. of labeled syn-hPRL bound to antibody. NSB=counts/min of bound in absence of antibody. T=total counts added per minute per tube. In four assays maximum binding corrected for NSB was from 12.86% to 13.96%.

hPRL levels expressed in picomoles/ml of 36 blood plasma samples having hPRL levels distributed through the range of the assay are determined (1) by relating the measured amount of unbound and bound labeled syn-hPRL to the hPRL standard curve and shown on the abscissa of the graph in FIG. 2 and (2) by relationship to the syn-hPRL curve, shown on the ordinate. The regression line has the slope of 1.09, a Y intercept of 1.20 and a correlation of 0.89 (Y=1.09X +1.20). Thus there is a very close correlation of hPRL values of sample obtained in relation to the two curves. To obtain the level of hPRL in nanograms/ml., the value in picomoles/ml. is multiplied by 23.

Because of the similarity of the standard curves, syn-hPRL can be substituted as a standard for hPRL in immunoassays. The usefulness of syn-hPRL as assay standards provides for greater reproducibility of the assay procedure over time because relatively large batches of syn-hPRL can be produced, compared to the size of batches of hPRL which can be practically obtained from human pituitary glands. Though the syn-hPRL gives a slightly different standard curve than hPRL, resulting in slightly different hPRL values for samples, the exactness of the actual amount of hPRL in a sample is less important than is reproducibility of results from one lab to another in order to demonstrate conclusively that either normal or abnormal amounts of hPRL are present in a sample.

It may be emphasized that the entire hPRL assay, including the raising of antibodies, may be accomplished without resorting to the use of purified natural hPRL. The antiserum that is raised against syn-hPRL-carrier is reactive with syn-hPRL and to a similar extent with the hPRL in the sample. Standard concentration of syn-hPRL in competition with a known concentration of labeled syn-hPRL for the binding sites of the antibodies in the antiserum provides a very reproducible standard curve. In sample mixtures, labeled syn-hPRL and samples are exposed to the antiserum so that the unknown concentrations of hPRL in the sample compete for the antibody binding sites with labeled syn-hPRL, and the amount of hPRL in the sample is determined according to the proportion of bound and unbound labeled syn-hPRL related to the standard curve prepared without using natural hPRL.

Antisera raised against syn-hPRL carrier are superior to antisera raised against hPRL because they exhibit no cross-reactivity with other pituitary substances, thereby contributing to reproducibility of assay results from one antiserum to another. Furthermore, antisera raised against syn-hPRL-carrier contain antibodies only reactive with a single antigenic determinant of hPRL, further contributing to reproducibility of the assay. Although antiserum raised against natural hPRL could also be used in the immunoassay, providing that the antiserum has sufficient binding sites reactive with the syn-hPRL, antiserum raised against natural hPRL is less desirable because it has far fewer sites reactive with syn-hPRL.

Labeled syn-hPRL is advantageous relative to labeled hPRL as a radioimmuno-marker because the synthetic peptide is much more readily radioiodinated than hPRL and is much more stable than radioiodinated hPRL. The greater degree of radioiodination contributes to higher counts in the bound and unbound fractions, thereby reducing experimental error.

Although the invention has been described in terms of certain preferred embodiments, modifications obvious to one with ordinary skill in the art may be made without departing from the scope of the invention. As mentioned above, a fragment of the hPRL N-terminal amino acid sequence may be used, providing that the fragment is antigenically active. Similarly, a longer synthetic peptide could be attached to a carrier, in which case the additional amino acids would not necessarily have to correspond to the natural hPRL sequence. It may also be possible that certain of the amino acids residues in the chain might be replaced with similar amino acids or modified amino acids, and such a modified peptide sequence might still retain hPRL antigenic activity. Modified peptide chains that when conjugated to carrier induce antisera reactive with hPRL are considered equivalents. The tyrosine which serves as a convenient means of linking the protein to a carrier might be eliminated (des-Tyr) if a carrier is used which is itself readily iodinated. Other methods of linking a protein segment to a carrier than with benzidine are known in the art and are considered equivalents. Other large non-immunogenic carrier molecules, such as long protein chains of repeating sequence, might be used as the carrier. Isotopes other than radioactive iodine, such as tritium, might be used to label syn-hPRL.

Although it is expected that antisera will generally be induced by in vivo innoculation of syn-hPRL-carrier into a host animal, in vitro inducement of antisera, e.g., by exposure of the conjugate to a spleen cell culture, is also contemplated. More specific antibodies may be obtained from the antibody-producing cells stimulated by the synthetic antigen by producing monoclonal antibodies through cell fusion or other cell immortalization techniques that are known in the art.

Various features of the invention are set forth in the following claims.

What is claimed is:

1. A method of preparing antiserum specific to human prolactin comprising
    preparing a synthetic antigen which simulates the antigenic properties of human prolactin, said synthetic antigen comprising a synthetic peptide and a relatively high molecular weight carrier that is conjugated to said peptide, said conjugate being of sufficient molecular weight to be recognized by the immunological system of a host animal, said peptide including a segment having the formula

Leu-Pro-Ile-Cys-Pro-Gly-Gly-Ala-Ala-Arg-Cys-Gln-X or a fragment of said segment which as part of said peptide-carrier conjugate acts to induce production of antibodies which specifically bind to human prolactin in a host animal, wherein X
    is Tyr or des-Tyr, immunizing a host animal with said synthetic antigen, and
    collecting antibody-containing serum produced by the immunological system of the host animal.

2. A method according to claim 1 wherein X is tyrosine.

3. A method according to claim 1 wherein said carrier has a molecular weight of greater than about 50,000.

4. A method according to claim 1 wherein said carrier is bovine serum albumin.

5. A method according to claim 1 wherein said peptide is linked to said carrier with benzidine.

6. A method according to claim 1 wherein said synthetic antigen has the formula:

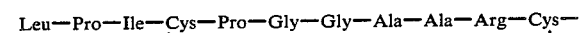

Leu—Pro—Ile—Cys—Pro—Gly—Gly—Ala—Ala—Arg—Cys—

—Gln—Tyr—NH—$C_6H_4$—$C_6H_4$—NH—bovine serum albumin.

7. A quantitative immunoassay for determining the level of human prolactin in a biological sample comprising
    providing a synthetic peptide that includes a segment having the formula

Leu-Pro-Ile-Cys-Pro-Gly-Gly-Ala-Ala-Arg-Cys-Gln-X or a fragment of said segment which reacts with an antibody that specifically binds to human prolactin, wherein X is Tyr or des-Tyr,
    providing an antiserum containing antibodies having binding sites which specifically bind with said peptide segment and with human prolactin,
    exposing the sample and said synthetic peptide to the antiserum in a manner such that said peptide and human prolactin in the sample compete for said binding sites,
    binding measuring the proportion of peptide bound to said sites, and
    determining the amount of human prolactin in the sample from the proportion of bound peptide.

8. An assay according to claim 7 including exposing aliquots of said antiserum to various known amounts of a substance selected from the group consisting of human prolactin and said peptide and also exposing said antiserum to a labeled form of said peptide, determining the proportion of bound labeled peptide in said aliquots, generating a standard curve based upon the proportion of bound labeled peptide in said aliquots, and calculating the amount of human prolactin in the sample from said standard curve.

9. An assay according to claim 7 including labeling said peptide with a radioactive isotope, separating bound from unbound labeled peptide and measuring the radioactivity of the bound or the unbound peptide.

10. An assay according to claim 7 wherein said X is tyrosine and said tyrosine is labeled with a radioactive isotope of iodine.

11. An assay according to claim 7 including conjugating said peptide to a high molecular weight carrier molecule and immunizing a host animal with said conjugate to raise the antiserum.

12. An assay according to claim 11 wherein said conjugate has the formula

Leu—Pro—Ile—Cys—Pro—Gly—Gly—Ala—Ala—Arg—Cys—

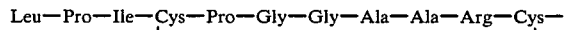

—Gln—Tyr—NH—C$_6$H$_4$—C$_6$H$_4$—NH—bovine serum albumin.

13. An assay according to claim 11 including exposing aliquots of the antiserum to various known concentrations of said peptide and also exposing said antiserum to a known concentration of a labeled form of said peptide, measuring the proportion of bound labeled peptide in the aliquots, generating a standard curve based on the proportion of bound labeled peptide in the aliquots and determining the amount of human prolactin in the serum sample from said standard curve.

14. A synthetic peptide which can be used as an antigen that induces the production of antibodies specific to human prolactin, which peptide includes the sequence having the formula:

Leu-Pro-Ile-Cys-Pro-Gly-Gly-Ala-Ala-Arg-Cys-Gln-X

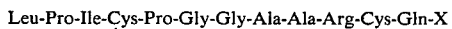

wherein X is selected from the group consisting of Tyr and des-Tyr or a fragment of said sequence which as a part of said synthetic peptide induces the production of antibody which specifically binds to human prolactin.

15. A synthetic peptide according to claim 14 labeled with a radioactive isotope.

16. A peptide according to claim 15 wherein said X is tyrosine, and said tyrosine is labeled with a radioactive isotope of iodine.

17. A composition comprising a synthetic peptide which can be used as an antigen that induces the production of anitbodies specific to human prolactin, which peptide includes the sequence having the formula:

Leu-Pro-Ile-Cys-Pro-Gly-Gly-Ala-Ala-Arg-Cys-Gln-X

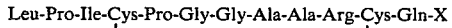

wherein X is selected from the group consisting of Tyr and des-Tyr or a fragment of said sequence which as a part of said synthetic peptide induces the production of antibody which specifically binds to human prolactin and a carrier to which said peptide is conjugated, said carrier being of sufficient molecular weight so that said conjugated peptide is recognized by the immunological system of a host animal.

* * * * *